US006267986B1

(12) United States Patent
Jain et al.

(10) Patent No.: US 6,267,986 B1
(45) Date of Patent: Jul. 31, 2001

(54) PROCESS FOR THE PREPARATION OF A CONTROLLED DRUG DELIVERY SYSTEM CONTAINING PSEUDOEPHEDRINE AND A LONG ACTING ANTIHISTAMINE

(75) Inventors: Girish Kumar Jain, Delhi; Ashok Rampal; Himadri Sen, both of Gurgaon, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/405,643

(22) Filed: Sep. 24, 1999

(51) Int. Cl.⁷ .................................... A61K 9/22; A61K 9/24
(52) U.S. Cl. .................... 424/472; 424/468; 424/469; 424/470; 424/474; 514/770; 514/779; 514/781; 514/782
(58) Field of Search ..................... 424/468, 472, 424/465, 469, 470, 473, 474, 479, 480

(56) References Cited

U.S. PATENT DOCUMENTS

| | | |
|---|---|---|
| 3,301,863 | 1/1967 | Villani .................................. 260/293 |
| 3,326,924 | 6/1967 | Uspo . |
| 3,357,986 | 12/1967 | Uspo . |
| 3,366,635 | 1/1968 | Uspo . |
| 3,419,565 | 12/1968 | Uspo . |
| 3,878,217 | 4/1975 | Carr et al. . |
| 4,219,559 | 8/1980 | Janssens et al. . |
| 4,282,233 | 8/1981 | Vilani et al. . |
| 4,369,184 | 1/1983 | Stokbroekx et al. . |
| 4,525,358 | 6/1985 | Baltes et al. . |
| 4,792,452 | 12/1988 | Howard et al. . |
| 4,990,535 | 2/1991 | Cho et al. ............................. 514/556 |
| 4,996,061 | 2/1991 | Webb et al. . |
| 5,100,675 | 3/1992 | Cho et al. ............................. 424/468 |

FOREIGN PATENT DOCUMENTS

| | | |
|---|---|---|
| 0811374 | 12/1997 | (EP) . |
| 9409761 | 5/1994 | (WO) . |
| 9853802 | 12/1998 | (WO) . |

*Primary Examiner*—James M. Spear
(74) *Attorney, Agent, or Firm*—Jayadeep R. Deshmukh, Esq.

(57) ABSTRACT

This invention relates to a process for the preparation of a controlled release pharmaceutical composition comprising two discrete zones wherein the first discrete zone comprises therapeutically effective amount of pseudoephedrine or its pharmaceutically acceptable salt as active ingredient and the second discrete zone comprises a therapeutically effective amount of a long-acting antihistamine selected from the group consisting of loratadine, azatidine, fexofenadine, terfenadine, cetirizine, astemizole, and levocabastine, or their pharmaceutically acceptable salt as active ingredient.

18 Claims, No Drawings

PROCESS FOR THE PREPARATION OF A CONTROLLED DRUG DELIVERY SYSTEM CONTAINING PSEUDOEPHEDRINE AND A LONG ACTING ANTIHISTAMINE

FIELD OF THE INVENTION

This invention relates to a process for the preparation of a controlled release pharmaceutical composition comprising two discrete zones wherein the first discrete zone comprises therapeutically effective amount of pseudoephedrine or its pharmaceutically acceptable salt as active ingredient and the second discrete zone comprises a therapeutically effective amount of a long-acting antihistamine selected from the group consisting of loratadine, azatidine, fexofenadine, terfenadine, cetirizine, astemizole, and levocabastine, or their pharmaceutically acceptable salt as active ingredient.

BACKGROUND OF THE INVENTION

Loratadine is disclosed in U.S. Pat. No. 4,282,233 as a non-sedating antihistamine useful, for example, in alleviation of seasonal allergic rhinitis symptoms such as sneezing and itching, and in the treatment of chronic idiopathic urticaria in patients six years or older. Loratadine is available in the form of conventional tablets that release loratadine in a conventional manner by the processes of disintegration and dissolution such that loratadine begins to elicit its antihistaminic effect within 1 to 3 hrs and the effect lasts in excess of 24 hrs. The tablets are thus orally administered only once daily.

Azatadine is disclosed in Belgian Patent No. 647,043 and in corresponding U.S. Pat. Nos. 3,326,924 and 3,419,565. The elimination half-life is reported to be 9–12 hrs. Terfenadine and fexofenadine are disclosed in U.S. Pat. No. 3,878,217 and have a duration of action of 12 to 24 hrs, and >24 hrs., respectively.

Cetirizine disclosed in U.S. Pat. No. 4,525,358; astemizole in U.S. Pat. No. 4,219,559, and levocabastine in U.S. Pat. No. 4,369,184; have a duration of action of 12 to 24 hrs, >24 hrs, and 16 to 24 hrs; respectively.

Pseudoephedrine and its pharmaceutically acceptable salts are well recognized by those skilled in the art as safe and effective nasal decongestants. Pseudoephedrine or its pharmaceutically acceptable salt when formulated as conventional tablets are commonly administered orally three or four times a day for the relief of nasal congestion. However, sustained release or controlled release tablets that release pseudoephedrine or its pharmaceutically acceptable salt at a controlled slow rate such that they may be administered twice-daily or once-daily are also commonly available.

It is well known to those skilled in the art that controlled delivery results in a decrease in the frequency of drug administration thereby improving patient compliance. Furthermore, controlled drug delivery systems produce constant therapeutic plasma levels of active ingredients as compared to fluctuations seen when multiple doses of a conventional formulation are given. Thus, controlled drug delivery systems may decrease the severity and frequency of side effects.

A decongestant is commonly administered orally in combination with an antihistamine for relieving nasal congestion associated with allergic rhinitis. It is quite apparent from the above stated facts that when the decongestant is pseudoephedrine or its pharmaceutically acceptable salt, and the antihistamine is a long-acting antihistamine, then the dosage form should preferably be designed such that the long acting antihistamine is released in a conventional manner and pseudoephedrine is released at a controlled rate such that the pharmaceutical composition is suitable for twice-daily or once-daily administration.

U.S. Pat. No. 4,996,061 discloses a pharmaceutical composition in the form of a multiple-compression tablet comprising of two discrete zones. The first discrete zone is made with formulation (A) comprising a therapeutically effective decongestant amount of a sympathomimetic drug, one or more pharmaceutically acceptable water-soluble non-ionic cellulose ethers in an amount from about 18% to about 50% by weight of formulation (A), and one or more pharmaceutically acceptable excipients. The second discrete zone is made with formulation (B) comprising a therapeutically effective antihistaminic amount of a piperidinoalkanol, calcium carbonate in an amount from about 0.5% to about 25% by weight of formulation (B), one or more pharmaceutically acceptable anionic surfactants in an amount from about 1% to about 10% by weight of formulation (B), and one or more pharmaceutically acceptable excipients. Formulation (B) may optionally contain a therapeutically effective decongestant amount of a sympathomimetic drug.

U.S. Pat. No. 4,792,452 discloses a tablet formulation composed of up to about 45% by weight of a pH-dependent salt of alginic acid, up to about 35% by weight of a pH-independent hydrocolloid gelling agent, binder and excipients. Release of the drug is therefore affected by the varying pH of the gastrointestinal Tract.

It is an object of the present invention to provide an oral controlled release pharmaceutical composition that releases the drug unaffected by the varying pH of the gastrointestinal Tract. The pharmaceutical composition in the form of tablets comprise a therapeutically effective amount of pseudoephedrine or its pharmaceutically acceptable salt and a therapeutically effective amount of a long-acting antihistamine selected from the group consisting of loratadine, azatadi, fexofenadine terfenadine, cetirizine, astemizole and levocabastine or their pharmaceutically acceptable salt such that the long-acting antihistamine or its pharmaceutically acceptable salt is released at a rapid rate, and pseudoephedrine or its pharmaceutically acceptable salt is released at a controlled rate.

Accordingly, the present invention provides a pharmaceutical composition in the form of a tablet comprising two discrete zones wherein the first zone comprises a therapeutically effective amount of pseudoephedrine or its pharmaceutically effective salt, one or more hydrophilic polymer(s) as herein described, a salt of a polyuronic acid, and a pharmaceutically acceptable salt of a group II metal ion; the second discrete zone comprises a therapeutically effective amount of a long-acting antihistamine selected from the group consisting of loratadine, azatidine, fexofenadine, terfenadine, cetirizine, astemizole, and levocabastine or their pharmaceutically acceptable salt with at least one pharmaceutically acceptable excipient. Optionally, the blend may be converted into granules by conventional means. Also optionally, the blend or the granulated blend may be compressed onto the first discrete zone. Further optionally, the blend may be coated onto the first discrete zone with the aid of a binder solution.

According to the present invention, the first discrete zone comprises one or more hydrophilic polymer(s). The hydrophilic polymer(s) that may be used in the present invention include cellulose ethers such as hydroxypropyl methylcellulose, hydroxypropylcellulose, or other water soluble or swellable polymers such as sodium carboxymethyl cellulose, xanthan gum, acacia, tragacanth gum, guar gum, karaya gum, alginates, gelatin, albumin and the like. The hydrophilic polymers used may also be polyacrylate polymers such as homopolymers based on acrylic acid crosslinked with allyl sucrose or allyl pentaerythritol, or copolymer based on acrylic acid and long chain ($C_{10}$–$C_{30}$) alkyl acrylates and cross-linked with allylpentaerythritol.

The preferred hydrophilic polymers are selected from the group consisting of hydroxypropyl methylcellulose, hydroxypropylcellulose, xanthan gum and mixtures thereof. The hydrophilic polymers may be present in an amount from about 0.1% to 90%, more preferably from about 20% to 50%, by weight of the total weight of the first discrete zone.

According to a more preferred embodiment of the present invention, the hydrophilic polymer is a mixture of a hydroxypropyl methylcellulose and hydroxypropylcellulose.

Examples of hydroxypropyl methylcellulose polymers that may be used in the present invention include those available from Dow Chemical Co. under the brand name Methocel, such as, Methocel K15M, Methocel K100M, and the like. Hydroxypropylcellulose polymers that may be used in the present invention include, for example, those available under the brand names Klucel™ from Aqualon and Nisso HPC™ from Nippon Soda Co. such as HPC-L™, HPC-M™, Klucel JF™, Klucel HF™, and the like. Preferably, the hydroxypropyl methylcellulose polymer is such that its 2% by weight aqueous solution has a viscosity greater than about 1,000 cPs, for example Methocel K4M with a viscosity of 4,000 cPs. More preferably, the hydroxypropyl methylcellulose is such that its 2% by weight aqueous solution has a viscosity greater than 10,000 cPs, for example, Methocel K15M and Methocel K100M whose 2% by weight aqueous solutions have viscosities of 15,000 cPs and 100,000 cPs, respectively.

The hydroxypropylcellulose polymers that may be used in the present invention include, for example, polymers available under the brand name Klucel™ and HPC™ available from Aqualon and Nippon Soda Co. Preferably the hydroxypropylcellulose polymer is such that it's 2% by weight aqueous solution has a viscosity less than 5,000 cPs, for example, HPC-H which has a viscosity of 1,000–4,000 cPs. More preferably, the hydroxypropylcellulose polymer is such that its 2% by weight aqueous solution has a viscosity less than 1,000 cPs, for example, HPC-M which has a viscosity of 150–400 cPs.

In another preferred embodiment of the present invention, the hydrophilic polymer is xanthan gum. Xanthan gum, also known as corn sugar gum, is a high molecular weight (ca $2 \times 10^6$) biosynthetic heteropolysaccharide gum produced by a pure-culture aerobic fermentation of a carbohydrate with Xanthomonas campestris. It is extraordinarily resistant to enzymatic degradation. Examples of xanthan gum that may be used in the present invention include those available from Merck & Co., KELCO Division under the trade name KELTROL™. In preferred embodiments of the present invention, xanthan gum has a particle size such that at least 50% by weight passes through a sieve with 44 µm mesh aperture (Sieve No. 325, ASTM). In more preferred embodiments, xanthan gum has a particle size such that all of it passes through a 44 µm mesh aperture (Sieve No. 325, ASTM).

According to the present invention, the first discrete zone comprises a salt of a polyuronic acid. Examples of water insoluble salts of a polyuronic acid include water insoluble group II metal ion salts of alginic acid, pectic acid and the like. In preferred embodiments of the present invention, the water insoluble group II metal ion salt is calcium alginate. The water insoluble group II metal ion salt of polyuronic acid may be present in an amount from about 4% to 90%, preferably from 8% to 20% by weight of the total weight of the first discrete zone.

Examples of water-soluble salts of polyuronic acid that may be used in the present invention include alkali metal salts of alginic acid, an alkali metal salt of pectic acid, and the like. In preferred embodiments of the present invention, the water-soluble salt of polyuronic acid is a salt of alginic acid, more preferably sodium alginate.

Examples of alkali metal salts of alginic acid that may be used in the present invention include sodium alginate, potassium alginate, ammonium alginate, and the like. In preferred embodiments the alginic salt is sodium alginate available from Merck & Co., KELCO Division under the trademark KELTONE® such as KELTONE® LVCR and KELTONE® HVCR. A mixture of the same or different viscosity grades of alginic acid salts may be used.

The water-soluble salt of polyuronic acid may be present in an amount from about 4% to about 90%, preferably from about 8% to about 20% by weight of the total weight of the first discrete zone.

An example of a complex salt of a polyuronic acid that may be used in the present invention is sodium calcium alginate such as available from Merck & Co., KELCO division under the trademark KELSET®. The sodium calcium alginate may be present in an amount from 4% to 90%, preferably from about 8% to 20% by weight of the total weight of the first discrete zone.

According to the present invention, the first discrete zone comprises a pharmaceutically acceptable salt of a group II metal ion. The pharmaceutically acceptable salt of a group II metal ion is used when the salt of polyuronic acid is water soluble but may not be used when the salt of polyuronic acid is water insoluble. The pharmaceutically acceptable salt of a group II metal ion that may be used in the present invention include water soluble salts of group II metal ions, such as calcium chloride, magnesium chloride, and the like, however, preferably the group II metal ion salt is a carbonate salt such as calcium or magnesium carbonate, more preferably calcium carbonate. The pharmaceutically acceptable group II metal ion salt may be used in an amount from about 2% to about 65%, preferably from about 5% to about 12% by weight of the total weight of the first discrete zone.

According to the process of the present invention the first discrete zone is prepared by mixing a therapeutically effective amount of pseudoephedrine or its pharmaceutically effective salt, one or more hydrophilic polymers, a salt of a polyuronic acid, and a pharmaceutically acceptable salt of a group II metal ion, and tableting the blend so obtained by conventional means; and wherein the second discrete zone is formed by mixing a therapeutically effective amount of a long-acting antihistamine selected from the group consisting of loratadine, azatadine, fexofenadine, terfenadine, cetirizine, astemizole, and levocabastine or their pharmaceutically acceptable salt with at least one pharmaceutically acceptable excipient, optionally converting the blend into granules by conventional means and either (a) compressing the blend or the granules onto the first discrete zone; or (b) coating the blend onto the first discrete zone with the aid of a binder solution.

The present invention is illustrated by the following examples. Alternatives will be apparent to those skilled in the art and are considered to be within the scope of the invention, and therefore the examples are not to be construed to restrict the invention.

EXAMPLE 1

This example illustrates the process of preparation of the pharmaceutical composition wherein the two discrete zones are two layers of a bilayer tablet. The first tablet layer was formed from ingredients given in Table 1.

TABLE 1

| Ingredient | Weight (mg/tablet) | % w/w |
|---|---|---|
| Pseudoephedrine sulfate | 240.00 | 40.00 |
| Microcrystalline cellulose (Avicel PH 101) | 15.00 | 2.50 |
| Xanthan gum (Keltrol TF) | 200.00 | 33.33 |
| Sodium alginate (Keltone HVCR) | 80.00 | 13.33 |
| Calcium carbonate | 53.00 | 8.83 |
| Magnesium Stearate | 6.00 | 1.00 |
| Colloidal silica (Aerosil 200) | 6.00 | 1.00 |
| Total | 600.00 | 100.00 |

Pseudoephedrine sulfate, microcrystalline cellulose, xanthan gum, sodium alginate, calcium carbonate, and half of the lubricants were mixed together and sieved through a sieve [British Standard Sieve (BSS No.44)]. The blend was compacted on a roll-compactor and the compact sieved through a sieve (BSS No.22) to obtain granules. The granules were mixed with the remaining lubricants and compressed into tablets to form the first tablet layer. The second tablet layer was formed from ingredients given in Table 2.

TABLE 2

| Ingredient | Weight (mg/tablet) | % w/w |
|---|---|---|
| Loratadine | 10.00 | 5.00 |
| Lactose | 95.00 | 47.50 |
| Microcrystalline Cellulose (Avicel pH 101) | 66.50 | 33.25 |
| Yellow Lake (FD&C 10) | 1.00 | 0.50 |
| Maize Starch | 20.00 | 10.00 |
| Starch (for starch paste) | 6.00 | 3.00 |
| Magnesium Stearate | 1.50 | 0.75 |
| Total | 200.00 | 100 |

Maize starch and Yellow Lake (FD&C 10) were sieved through BSS No.100 sieve and mixed with loratadine, microcrystalline cellulose and lactose each individually sieved through a sieve with 600 μm mesh aperture (BSS No. 25). The powder blend was granulated with starch paste (10% w/w). The dried granules were blended with magnesium stearate and compressed into tablets.

The dissolution of pseudoephedrine from the tablets is given in Table 3.

TABLE 3

| Time (hr) | Cumulative percent dissolved |
|---|---|
| 1 | 22.2 ± 0.6 |
| 2 | 34.9 ± 0.9 |
| 4 | 53.6 ± 1.5 |
| 6 | 66.9 ± 2.4 |
| 8 | 76.7 ± 2.9 |
| 12 | 88.4 ± 2.8 |
| 16 | 93.1 ± 2.2 |

EXAMPLE 2

This example illustrates the process of preparation of the pharmaceutical compositon wherein the two discrete zones are two layers of a bilayer tablet. The first tablet layer was formed from ingredients given in Table 4.

TABLE 4

| Ingredient | Weight (mg/tablet) | % w/w |
|---|---|---|
| Pseudoephedrine sulfate | 240.00 | 40.00 |
| Microcrystalline cellulose (Avicel PH 101) | 15.00 | 2.50 |
| Xanthan gum (Keltrol TF) | 200.00 | 33.33 |
| Sodium alginate (Keltone LVCR) | 80.00 | 13.33 |
| Calcium carbonate | 53.00 | 8.83 |
| Magnesium Stearate | 6.00 | 1.00 |
| Colloidal silica (Aerosil 200) | 6.00 | 1.00 |
| Total | 600 | 100 |

The first tablet layer was prepared as described in Example 1. The second tablet layer was prepared according to the composition given in the Table 2 according to the process described in Example 1. The dissolution of pseudoephedrine from the tablet is given in Table 5.

TABLE 5

| Time (hr) | Cumulative percent dissolved |
|---|---|
| 1 | 23.5 ± 0.17 |
| 2 | 36.1 ± 0.42 |
| 4 | 54.2 ± 1.08 |
| 6 | 67.5 ± 1.79 |
| 8 | 77.4 ± 1.96 |
| 12 | 88.6 ± 1.80 |
| 16 | 92.3 ± 1.40 |

EXAMPLE 3

This example illustrates the process of preparation of the pharmaceutical compostion wherein the two discrete zones are two layers of a bilayer tablet. The first tablet layer was formed from ingredients given in Table 6.

TABLE 6

| Ingredient | Weight (mg/tablet) | % w/w |
|---|---|---|
| Pseudoephedrine sulfate | 240.00 | 40.00 |
| Microcrystalline cellulose (Avicel PH 101) | 15.00 | 2.50 |
| Hydroxypropylcellulose (HPC-H) | 200 | 33.33 |
| Sodium alginate (Keltone HVCR) | 80.00 | 13.33 |
| Calcium carbonate | 53.00 | 8.83 |
| Magnesium Stearate | 6.00 | 1.00 |
| Colloidal silica (Aerosil 200) | 6.00 | 1.00 |
| Total | 600.00 | 100.00 |

The first tablet layer was prepared as described in Example 1. The second tablet layer was prepared according to the composition given in Table 2 according to the process described in Example 1. The dissolution of pseudoephedrine from the Tablet is given in Table 7.

TABLE 7

| Time (hr) | Cumulative percent dissolved |
|---|---|
| 1 | 27.5 ± 0.30 |
| 2 | 39.4 ± 0.92 |

TABLE 7-continued

| Time (hr) | Cumulative percent dissolved |
|---|---|
| 4 | 56.6 ± 1.40 |
| 6 | 69.1 ± 1.75 |
| 8 | 78.5 ± 1.96 |
| 12 | 90.2 ± 2.16 |
| 16 | 95.9 ± 2.40 |

EXAMPLE 4

This example illustrates the process of preparation of the pharmaceutical compostion wherein the two discrete zones are two layers of a bilayer tablet. The first tablet layer was formed from ingredients given in Table 8.

TABLE 8

| Ingredient | Weight (mg/tablet) | % w/w |
|---|---|---|
| Pseudoephedrine sulfate | 240.00 | 40.00 |
| Microcrystalline cellulose (Avicel PH 101) | 15.00 | 2.50 |
| Hydroxypropylmethyl cellulose (Methocel K-15M CR) | 150.00 | 25.00 |
| Hydroxypropylcellulose (HPC-M) | 50.00 | 8.33 |
| Sodium alginate (Keltone HVCR) | 80.00 | 13.33 |
| Calcium carbonate | 55.00 | 9.16 |
| Magnesium Stearate | 5.00 | 0.84 |
| Colloidal silica (Aerosil 200) | 5.00 | 0.84 |
| Total | 600.00 | 100.00 |

The first tablet layers was prepared as described in Example 1. The second tablet layer was prepared according to the composition given in Table 2 and according to the process according to the process described in Example 1. The dissolution of pseudoephedrine from the tablet is given in Table 9.

TABLE 9

| Time (hr) | Cumulative percent dissolved |
|---|---|
| 1 | 26.2 ± 0.60 |
| 2 | 35.0 ± 1.00 |
| 4 | 51.0 ± 1.50 |
| 6 | 63.0 ± 1.70 |
| 8 | 71.7 ± 2.40 |
| 12 | 84.0 ± 2.80 |
| 16 | 89.40 ± 1.90 |

EXAMPLE 5

This example illustrates the process of preparation of the pharmaceutical compostion wherein the two discrete zones are two layers of a bilayer tablet. The first tablet layer was formed from ingredients given in Table 10.

TABLE 10

| Ingredient | Weight (mg/tablet) | % w/w |
|---|---|---|
| Pseudoephedrine sulfate | 240.00 | 42.48 |
| Hydroxypropylmethyl cellulose (Methocel K-100M CR) | 150.00 | 26.55 |
| Hydroxypropylcellulose (HPC-M) | 50.00 | 8.85 |
| Sodium alginate (Keltone HVCR) | 70.00 | 12.38 |

TABLE 10-continued

| Ingredient | Weight (mg/tablet) | % w/w |
|---|---|---|
| Calcium carbonate | 45.00 | 7.96 |
| Magnesium Stearate | 4.00 | 0.708 |
| Colloidal silica (Aerosil 200) | 6.00 | 1.062 |
| Total | 565.00 | 100.00 |

The first tablet layer was prepared as described in Example 1. The second tablet layer was prepared according to the composition given in Table 2 and according to the process described in Example 1. The dissolution of pseudoephedrine from the tablet is given in Table 11.

TABLE 11

| Time (hr) | Cumulative percent dissolved |
|---|---|
| 1 | 25.5 ± 0.90 |
| 2 | 36.9 ± 1.50 |
| 4 | 53.0 ± 1.60 |
| 6 | 65.0 ± 1.40 |
| 8 | 74.6 ± 1.30 |
| 12 | 88.3 ± 30.0 |
| 16 | 95.4 ± 0.30 |

EXAMPLE 6

This example illustrates the process of preparation of the pharmaceutical compostion wherein the two discrete zones are two layers of a bilayer tablet. The first tablet layer was formed from ingredients given in Table 12.

TABLE 12

| Ingredient | Weight (mg/tablet) | % w/w |
|---|---|---|
| Pseudoephedrine sulfate | 240.00 | 42.48 |
| Microcrystalline cellulose (Avicel PH 101) | 15.00 | 2.65 |
| Hydroxypropylmethyl cellulose (Methocel K-15M CR) | 150.00 | 26.55 |
| Sodium alginate (Keltone HVCR) | 100.00 | 17.7 |
| Calcium carbonate | 50.00 | 8.85 |
| Magnesium Stearate | 4.00 | 0.708 |
| Colloidal silica (Aerosil 200) | 6.00 | 1.062 |
| Total | 565.00 | 100.00 |

The first tablet layer was prepared as described in Example 1. The second tablet layer was prepared according to the composition given in Table 2 and according to the porcess described in Example 1. The dissolution of pseudoephedrine from the tablet is given in Table 13.

TABLE 13

| Time (hr) | Cumulative percent dissolved |
|---|---|
| 1 | 26.8 ± 0.26 |
| 2 | 37.7 ± 0.40 |
| 4 | 58.0 ± 1.60 |
| 6 | 72.0 ± 2.40 |
| 8 | 79.7 ± 2.20 |
| 12 | 93.6 ± 1.40 |
| 16 | 97.5 ± 1.20 |

EXAMPLE 7

This example illustrates the process of preparation of the pharmaceutical compostion wherein the two discrete zones are two layers of a bilayer tablet. The first tablet layer was formed from ingredients given in Table 14.

TABLE 14

| Ingredient | Weight (mg/tablet) | % w/w |
| --- | --- | --- |
| Pseudoephedrine sulfate | 240.00 | 40.00 |
| Microcrystalline cellulose (Avicel PH 101) | 15.00 | 2.50 |
| Hydroxypropylmethyl cellulose (Methocel K-15M CR) | 170.00 | 28.33 |
| Hydroxypropylcellulose (HPC-M) | 50.00 | 8.33 |
| Sodium alginate (Keltone HVCR) | 70.00 | 11.67 |
| Calcium carbonate | 45.00 | 7.50 |
| Magnesium Stearate | 4.00 | 0.67 |
| Colloidal silica (Aerosil 200) | 6.00 | 1.00 |
| Total | 600.00 | 100.00 |

The first tablet layer was prepared as described in Example 1. The second tablet layer was prepared according to the composition given in Table 2 and according to the process described in Example 1. The dissolution of pseudoephedrine from the tablet is given in Table 15.

TABLE 15

| Time (hr) | Cumulative percent dissolved |
| --- | --- |
| 1 | 26.9 ± 0.8 |
| 2 | 37.8 ± 1.4 |
| 4 | 53.2 ± 0.2 |
| 6 | 64.1 ± 1.6 |
| 8 | 72.7 ± 2.0 |
| 12 | 85.3 ± 2.4 |
| 16 | 92.4 ± 2.5 |

EXAMPLE 8

This example illustrates the process of preparation of the pharmaceutical compostion wherein the two discrete zones are two layers of a bilayer tablet. The first tablet was formed from ingredients given in Table 16.

TABLE 16

| Ingredient | Weight (mg/tablet) | % w/w |
| --- | --- | --- |
| Pseudoephedrine sulfate | 240.00 | 33.71 |
| Microcrystalline cellulose (Avicel PH 101) | 15.00 | 2.42 |
| Hydroxypropylmethyl cellulose (Methocel K-15M CR) | 190.00 | 30.65 |
| Hydroxypropylcellulose (HPC-M) | 50.00 | 8.06 |
| Sodium alginate (Keltone HVCR) | 70.00 | 11.29 |
| Calcium carbonate | 45.00 | 7.26 |
| Magnesium Stearate | 4.00 | 0.645 |
| Colloidal silica (Aerosil 200) | 6.00 | 0.967 |
| Total | 620.00 | 100.00 |

The first tablet layer was prepared as described in Example 1. The second tablet layer was prepared according to the composition given in Table 2 and according to the process described in Example 1. The dissolution of pseudoephedrine from the tablet is given in Table 17.

TABLE 17

| Time (hr) | Cumulative percent dissolved |
| --- | --- |
| 1 | 26.0 ± 0.7 |
| 2 | 36.6 ± 1.8 |
| 4 | 52.0 ± 2.0 |
| 6 | 63.9 ± 2.2 |
| 8 | 72.6 ± 2.5 |
| 12 | 85.5 ± 3.0 |
| 16 | 92.5 ± 3.0 |

EXAMPLE 9

This illustrates the process of preparation of the pharmaceutical compostion wherein the two discrete zones are two layers of a bilayer tablet. The first tablet layer was formed from ingredients given in Table 18.

TABLE 18

| Ingredient | Weight (mg/tablet) | % w/w |
| --- | --- | --- |
| Pseudoephedrine sulfate | 240.00 | 40.00 |
| Microcrystalline cellulose (Avicel PH 101) | 15.00 | 2.50 |
| Hydroxypropylmethyl cellulose (Methocel K-15M CR) | 150.00 | 25.00 |
| Hydroxypropylcellulose (HPC-M) | 50.00 | 8.33 |
| Sodium calcium alginate (KELSET) | 133.00 | 22.17 |
| Magnesium Stearate | 6.00 | 1.00 |
| Colloidal silica (Aerosil 200) | 6.00 | 1.00 |
| Total | 600.00 | 100.00 |

The first tablet layer was prepared as described in Example 1. The second tablet layer was prepared according to the composition given in Table 2 and according to the process described in Example 1. The dissolution of pseudoephedrine from the tablet is given in Table 19.

TABLE 19

| Time (hr) | Cumulative percent dissolved |
| --- | --- |
| 1 | 31.8 ± 0.60 |
| 2 | 46.6 ± 0.90 |
| 4 | 67.0 ± 2.70 |
| 6 | 81.7 ± 1.60 |
| 8 | 91.1 ± 1.90 |
| 12 | 101.9 ± 2.20 |

We claim:

1. A process for the preparation of a pharmaceutical composition in the form of a tablet comprising two discrete zones wherein the first zone is formed by mixing a therapeutically effective amount of pseudoephedrine or its pharmaceutically effective salt, one or more hydrophilic polymer(s), a salt of a polyuronic acid and a pharmaceutically acceptable salt of a group II metal ion and tableting the blend so obtained; wherein the second discrete zone is formed by mixing a therapeutically effective amount of a long-acting antihistamine selected from the group consisting of loratadine, azatadine, fexofenadine, terfenadine, cetirizine, astemizole, and levocabastine or their pharmaceutically acceptable salt with at least one pharmaceutically acceptable excipient, and optionally converting the blend into granules and either (a) compressing the blend or the granules onto the first discrete zone or (b) coating the blend onto the first discrete zone with the aid of a binder solution.

2. A process as claimed in claim 1 wherein the hydrophilic polymers are selected from the class of cellulose ethers.

3. A process as claimed in claim 2 wherein the cellulose ether is selected from the group consisting of hydroxypropylmethylcellulose, hydroxypropylcellulose, and mixtures thereof.

4. A process as claimed in claim 3 wherein the hydroxypropyl methylcellulose is such that it's 2% by weight aqueous solution has a viscosity greater than 10,000 cPs and the hydroxypropylcellulose is such that it's 2% by weight aqueous solution has a viscosity less than 5,000 cPs.

5. A process as claimed in claim 1 wherein the hydrophilic polymer is xanthan gum.

6. A process as claimed in claim 1 wherein the salt of a polyuronic acid is calcium alginate.

7. A process as claimed in claim 1 wherein the salt of a polyuronic acid is sodium alginate.

8. A process as claimed in claim 1 wherein the salt of a polyuronic acid is sodium calcium alginate.

9. A process as claimed in claim 1 wherein the salt of a group II metal ion is calcium carbonate.

10. A pharmaceutical composition in the form of a tablet comprising two discrete zones; wherein the first zone comprises a therapeutically effective amount of pseudoephedrine or its pharmaceutically effective salt, one or more hydrophilic polymer(s), a salt of a polyuronic acid and a pharmaceutically acceptable salt of a group II metal ion; wherein the second discrete zone comprises an effective amount of a long-acting antihistamine selected from the group consisting of loratadine, azatadine, fexofenadine, terfenadine, cetirizine, astemizole, and levocabastine or their pharmaceutically acceptable salt with at least one pharmaceutically acceptable excipient.

11. The composition as claimed in claim 10 wherein the hydrophilic polymers are selected from the class of cellulose ethers.

12. The composition as claimed in claim 11 wherein the cellulose ether is selected from the group consisting of hydroxypropylmethylcellulose, hydroxypropylcellulose, and mixtures thereof.

13. The composition as claimed in claim 12 wherein the hydroxypropylmethylcellulose is such that it's 2% by weight aqueous solution has a viscosity greater than 10,000 cPs and the hydroxypropylcellulose is such that it's 2% by weight aqueous solution has a viscosity less than 5,000 cPs.

14. The composition as claimed in claim 10 wherein the hydrophilic polymer is xanthan gum.

15. The composition as claimed in claim 10 wherein the salt of a polyuronic acid is calcium alginate.

16. The composition as claimed in claim 10 wherein the salt of a polyuronic acid is sodium alginate.

17. The composition as claimed in claim 10 wherein the salt of a polyuronic acid is sodium calcium alginate.

18. The composition as claimed in claim 10 wherein the salt of a group II metal ion is calcium carbonate.

* * * * *